United States Patent [19]

Temple, Jr.

[11] Patent Number: 4,581,357

[45] Date of Patent: * Apr. 8, 1986

[54] ANTIPSYCHOTIC 5-FLUORO-PYRIMIDIN-2-YL PIPERAZINE COMPOUND

[75] Inventor: Davis L. Temple, Jr., Evansville, Ind.

[73] Assignee: Mead Johnson & Company, Evansville, Ind.

[ * ] Notice: The portion of the term of this patent subsequent to Dec. 27, 2000 has been disclaimed.

[21] Appl. No.: 593,347

[22] Filed: Mar. 26, 1984

Related U.S. Application Data

[63] Continuation-in-part of Ser. No. 464,275, Feb. 7, 1983, abandoned.

[51] Int. Cl.⁴ .................. C07D 401/14; C07D 401/06; C07D 403/04; A61K 31/505
[52] U.S. Cl. .................................... 514/253; 544/230; 544/295
[58] Field of Search .................. 544/230; 424/251; 514/253

[56] References Cited

U.S. PATENT DOCUMENTS

| | | | |
|---|---|---|---|
| 3,398,151 | 8/1968 | Wu et al. | 260/268 |
| 3,717,634 | 2/1973 | Wu et al. | 260/256 |
| 3,907,801 | 9/1975 | Wu et al. | 260/268 |
| 3,976,776 | 8/1976 | Wu et al. | 424/251 |
| 4,182,763 | 1/1980 | Casten et al. | 424/251 |
| 4,423,049 | 12/1983 | Temple, Jr. | 424/251 |

OTHER PUBLICATIONS

Y. H. Wu, et al., *J. Med. Chem.*, 15/5, 477–479 (1972).
Y. H. Wu, et al., *Journal Medicinal Chemistry*, 12/4, 876–881 (1969).

*Primary Examiner*—Mark L. Berch
*Attorney, Agent, or Firm*—Richard P. Ryan; Robert H. Uloth

[57] ABSTRACT

8-[4-[4-(5-Fluoro-pyrimidin-2-yl)-1-piperazinyl]butyl]-8-azaspiro[4.5]decane-7,9-dione and its pharmaceutically acceptable salts demonstrate antipsychotic activity.

3 Claims, No Drawings

ANTIPSYCHOTIC 5-FLUORO-PYRIMIDIN-2-YL PIPERAZINE COMPOUND

CROSS-REFERENCE TO RELATED APPLICATION

This is a continuation-in-part of co-pending application U.S. Ser. No. 464,275 filed Feb. 7, 1983, now abandoned.

FIELD OF THE INVENTION

This invention involves drug, bio-affecting, and body-treating compositions and methods employing a heterocyclic organic compound of the pyrimidine series as active ingredient (Class 424, Subclass 251).

BACKGROUND OF THE INVENTION

Related art may be viewed in light of the following structural formula (1):

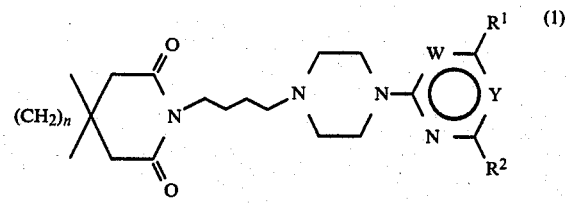

in which n is 4 to 5 and W and Y are different, one being CH and the other being N; $R^1$ and $R^2$ are independently selected from a group of substituents consisting of, among other moieties, hydrogen and halogen.

Wu, et al., discloses tranquilizing compounds of this structural type in *J. Med. Chem.*, 15/5, 477–479 (1972) and in U.S. Pat. No. 3,717,634 patented Feb. 20, 1973. Additionally, three 5-substituted pyrimidinyl derivatives were disclosed. These correspond to the above structural formula wherein W is N and Y is C—NO$_2$, C—NHSO$_2$C$_4$H$_9$ and C—OH. No 5-halogenopyrimidines were specifically disclosed or claimed.

The following group of references represent related but less pertinent art.

Wu, et al., U.S. Pat. No. 3,907,801, issued Sept. 23, 1975, is a divisional of the above-cited '634 Wu patent. U.S. Pat. No. 3,907,801 claims the pyridinyl compound subject matter (e.g. W and Y are both CH).

Wu, et al., U.S. Pat. No. 3,976,776, issued Aug. 24, 1976, is also a divisional which claims the use of these compounds in a tranquilizing process.

Casten, et al., U.S. Pat. No. 4,182,763, issued Jan. 8, 1980, discloses and claims the use of buspirone (2), a specific compound of the above series, for treating anxiety.

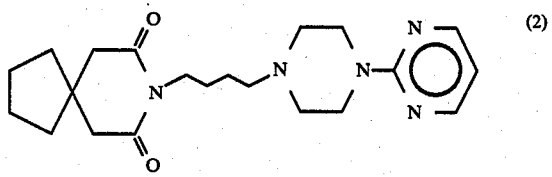

Wu, U.S. Pat. No. 3,398,151, issued Aug. 20, 1968, discloses and claims related compounds wherein the pyrimidine ring has been replaced by a phenyl moiety, unsubstituted or substituted (e.g., halogen).

Wu, et al., *Journal Medicinal Chemistry*, 12/4, 876–881 (1969) also reports work done with these phenyl analogs. No fluoro substituted phenyl derivatives are listed as examples or in any of the tables.

Finally, Temple, U.S. Pat. No. 4,423,049, issued Dec. 27, 1983, discloses and claims a series of 1-[4-(4,4-dialkyl-2,6-piperidinedion-1-yl)butyl]piperazines with 2-pyrimidinyl substituents in the 4-position which demonstrate useful anxiolytic properties. The pyrimidine ring in this series of compounds may either be unsubstituted or monosubstituted bearing a fluoro, chloro, hydroxyl, or trifluoromethyl substituent.

The present invention involves the discovery that the previously unsynthesized compound 8-[4-[4-(4-fluoro-pyrimidin-2-yl)-1-piperazinyl]butyl]-8-azaspiro[4.5]decane-7,9-dione possesses long acting antipsychotic activity. This pharmacological activity sets the instant invention apart from related pyrimidinyl compounds of the above references. These reference compounds mainly act as anxiolytics, with only minor antipsychotic action and that of short duration.

SUMMARY OF THE INVENTION

8-[4-[4-(5-Fluoro-pyrimidin-2-yl)-1-piperazinyl]butyl]-8-azaspiro[4.5]decane-7,9-dione (I), hereinafter referred to as MJ 14594, and its pharmaceutically acceptable salts have been demonstrated to possess useful antipsychotic activity with a good duration of action. This compound has the following structural formula:

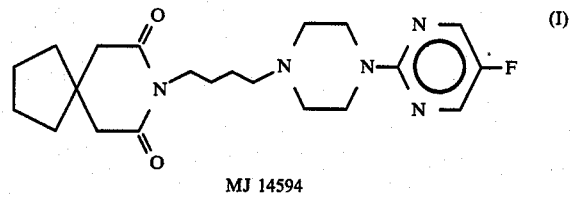

MJ 14594

DETAILED DESCRIPTION OF THE INVENTION

A unitary process comprehending several method embodiments (A, B and C) may be employed for preparation of the Formula I compound, MJ 14594. Variations of the methods to produce the same compounds in somewhat different fashion will also be evident to one skilled in the art. Examples will be given for specific illustration of the preferred embodiment.

UNITARY PROCESS

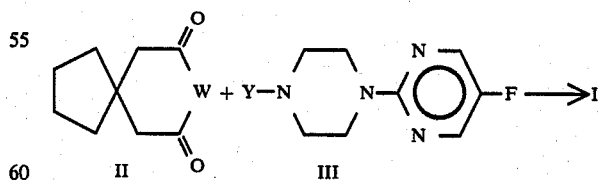

In the above scheme, the symbol "W" can be

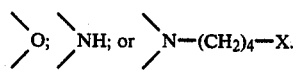

The symbol "Y" can be H₂N—(CH₂)₄—; X—(CH₂)₄—;

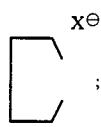

or H—. The relationship between W and Y Is:

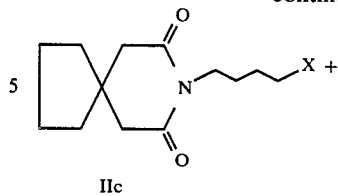
IIc

| Method No. | A | B | C |
|---|---|---|---|
| when W is: | >O (IIa) | >NH (IIb) | >N—(CH₂)₄—X (IIc) |
| then Y is: | H₂N—(CH₂)₄— (IIIa) | X—(CH₂)₄— (IIIb) or [Xθ ring] (IIIb') | H (IIIc) |

The symbol "X" refers to a suitable displacement group such as chloride, bromide, iodide, sulfate, phosphate, tosylate, or mesylate. In practice, intermediate compound IIIb readily converts to IIIb', the only species which can be isolated. For use as intermediates, the two compounds are equivalent.

Method A

Method B

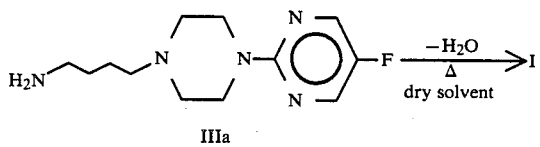

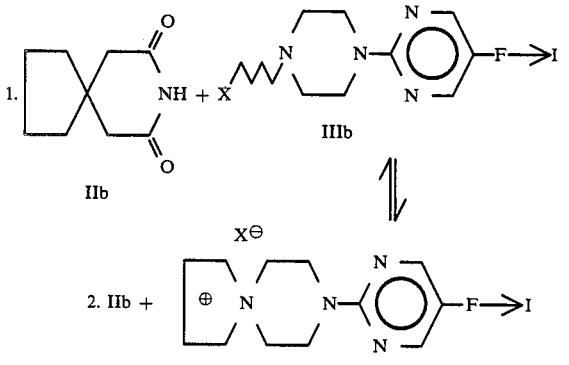

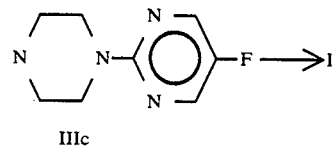
IIIc

The condensation process in Method A is carried out by refluxing the reactants in a dry, inert reaction medium such as pyridine or xylene. For Methods B and C the process is carried out under reaction conditions suitable for the preparation of tertiary amines by alkylation of secondary amines. The reactants are heated in a suitable organic liquid at temperatures of about 60° C. to about 150° C. in the presence of an acid binding agent. Benzene, dimethylformamide, ethanol, acetonitrile, toluene, and n-butyl alcohol are preferred examples of the organic liquid reaction media. The preferred acid binding agent is potassium carbonate, but other inorganic and tertiary organic bases may be employed including other alkali and alkylene earth metal carbonates, bicarbonates, or hydrides, and the tertiary amines. All three methods have been adequately described by Wu, et al in the cited patents and articles listed above and these are hereby incorporated in entirety by reference.

As an example of a method variation to produce the same compounds somewhat differently, an N-substituted [4-(1-piperazinyl)butyl]azaspirodecanedione (V) can be reacted with an appropriate pyrimidine system to yield the product of Formula I, e.g.

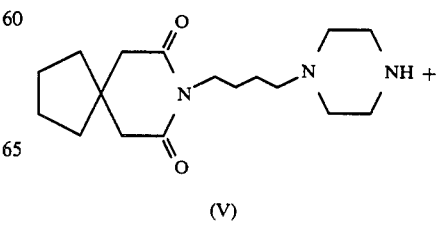
(V)

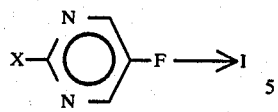

From this variation is derived the currently preferred method, described hereinafter, for preparation of I.

The intermediate spiro glutaric acid anhydrides or imides of Formula II are either commercially available, found in the above references, or described herein.

Pyrimidinylpiperazine intermediates (III) are described in the aforementioned Wu, et al patents and certain references cited therein. Although these procedures are applicable to the preparation of 5-fluoropyrimidinyl piperazine intermediates not specifically disclosed therein but which are required as intermediates for the present invention, a representative synthesis of IIIc is given as a working example for further exemplification. Intermediates IIIa and IIIb are readily obtainable from IIIc using the standard methods shown by Wu, et al.

MODEL SYNTHESIS OF (IIIc)

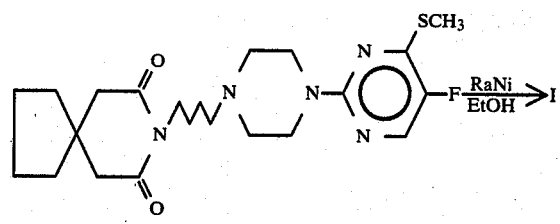

The distinguishing psychotropic profile displayed by MJ 14594 was determined by results of the following screening tests. MJ 14594 is approximately three times more potent than buspirone in the conditioned avoidance response test according to method described in the Wu, et al patents and publications, supra.

This test method utilizes orally treated fasted rats and generally reflects tranquilizing activity of a compound without necessarily differentiating anxiolytic from antipsychotic compounds. Of even greater interest was the finding that MJ 14594, given at 35 mg/kg p.o. had an approximately three-fold increase in duration compared with buspirone given at 100 mg/kg, p.o.

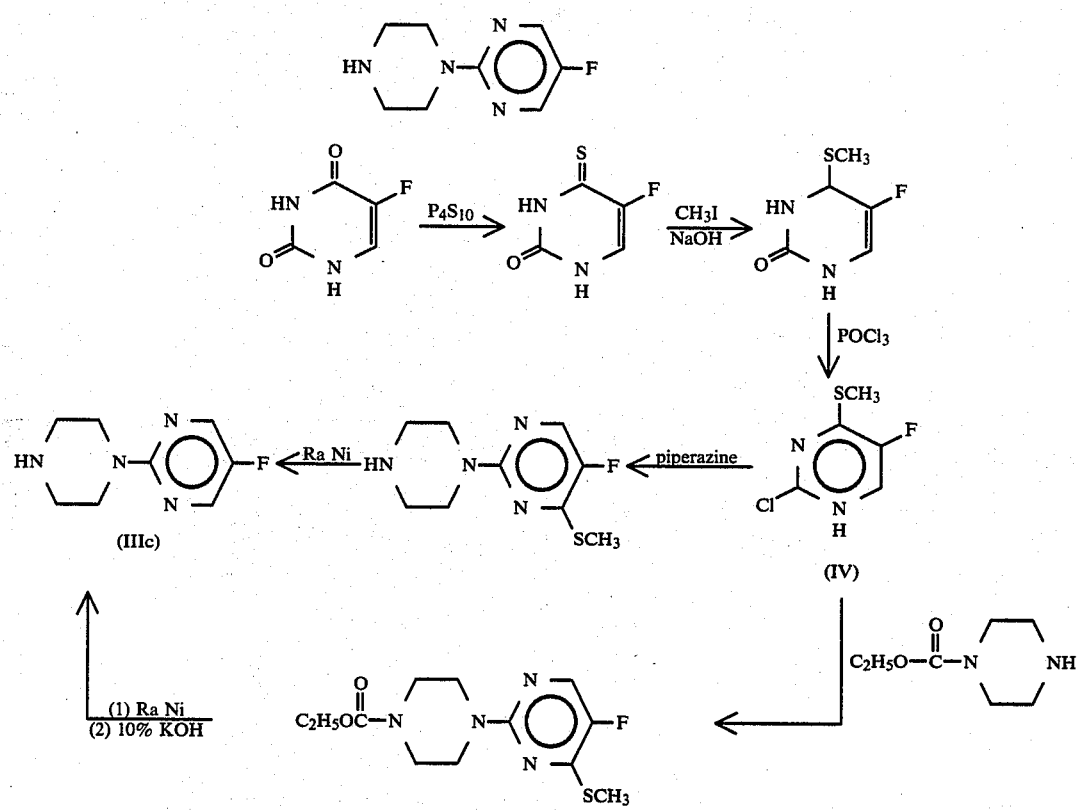

This synthetic scheme begins with 5-fluorouracil and proceeds by known reactions to the desired piperazine intermediate. Although the route via carbethoxypiperazine is more involved, the higher yield of IIIc without by-products makes it somewhat superior.

In practice, it was found preferable to prepare I from IV and V as shown in the following scheme.

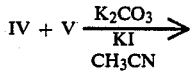

A more definitive test for antipsychotic efficacy is the apomorphine stereotypy behavior test in nonfasted rats. This test determines the ability of centrally active compounds to block apomorphine induced stereotyped behavior. This preclinical test is a useful indicator of potential antipsychotic efficacy (Janssen, et al, *Arzneimittel-Forsch.*, 17:841 (1966)). While MJ 14594 was roughly equipotent with buspirone in this blockade of apomorphine stereotypy test, its activity was maintained for over 6 hours versus a 1 to 2 hour duration for buspirone in this test.

Antipsychotic drugs are believed to control the symptomatology of psychosis by acting as postsynaptic dopamine receptor antagonists. Since the stereotypy blockade test is reflective of dopamine antagonist activity, comparison of duration of action for the two drugs indicates that the antagonist component (antipsychotic action) of MJ 14594 perseveres while that of buspirone is rapidly diminished.

Additional support for classifying MJ 14594 as an antipsychotic agent is obtained from radioreceptor binding studies. Radioreceptor binding assays which measure the inhibition of binding of various neuronally active molecules are used to more specifically define tranquilizing activity. Although MJ 14594 has only 10-20% of the binding affinity of buspirone for dopaminergic receptors, it appears to be much more antagonist-like in nature. The binding affinity of buspirone at [H$^3$]spiperone-labeled receptors decreases in the presence of 5 μM guanine triphosphate (GTP) while that of MJ 14594 is essentially unchanged. Such a GTP-induced shift in binding indicates agonist activity whereas the lack of a shift is associated with antagonist action. Additional background associated with dopamine receptor binding assays and their reflections of antipsychotic activity may be found in the following references: Burt, Creese, and Snyder, *Molecular Pharmacology*, 12:800 (1976); Burt, Creese, and Snyder, *Science*, 196:326 (1977); Creese, Burt, and Snyder, *Science*, 192:481 (1976); Creese, Prosser, and Snyder, *Life Science*, 23:495 (1978); Creese and Snyder, *European Journal of Pharmacology*, 50:459 (1978); Creese, Usdin, and Snyder, *Nature*, 278:577 (1979).

Testing of MJ 14594 in the rat Vogel model, an anxiolytic behavioral paradigm, demonstrates that the compound lacks activity at doses below 5 mg/kg whereas buspirone is active at a level of 1.0 mg/kg in this anxiolytic screening test. The rat Vogel model is a modification of the Vogel Conflict test which is a reliable conflict procedure for testing antianxiety agents (Vogel, Beer, and Clody, *Psychopharmacologia* (Berl.) 21, 1-7 (1971)).

Additional data have been obtained from comparative testing in other CNS screening methods. MJ 14594 does not induce catalepsy at doses up to 70 mg/kg (higher dose levels cause toxicity) but unlike buspirone does not reverse trifluoperazine-induced catalepsy. Tested against standard antipsychotic agents in a recently developed monkey model (model described in Kovacic, Domino, *J. Clin. Psychopharmacol.*, 2:305-307, 1982), MJ 14594 appeared to lack the potential for development of clinical side effects, such as extrapyramidal symptoms. Accordingly, MJ 14594 would offer a significant therapeutic advantage over most other established antipsychotic agents. MJ 14594 displays a cat cortical electroencephalogram pattern similar to but indicative of greater potency than buspirone. Table 1 (following) sets forth a comparative tabulation of MJ 14594 and buspirone data.

| | COMPARATIVE TEST DATA MJ 14594 vs. BUSPIRONE | |
|---|---|---|
| Test | Utility | Result |
| 1. Conditioned Avoidance Response | measures general tranquilizing activity | MJ 14594 at 35 mg/kg p.o. has 3× duration of action of buspirone given at 100 mg/kg p.o. |
| 2. Apomorphine Stereotypy Behavior | indicates antipsychotic action | MJ 14594 active for >6 hrs. buspirone active for only 1-2 hours. |
| 3. Receptor Binding | more specifically defines mechanism of tranquilizing activity | MJ 14594 more a dopamine antagonist (antipsychotic) where buspirone more a dopamine agonist. |
| 4. Vogel Model | selective anxiolytic activity | MJ 14594 has activity at levels >5.0 mg/kg p.o. buspirone active at 1.0 mg/kg p.o. |
| 5. Catalepsy Reversal | non-antipsychotic profile (No known antipsychotic reverses catalepsy) | MJ 14594 inactive (antipsychotic) buspirone active. |

In summary, the in vivo potency, long duration of action, lack of side-effect potential, and antagonist-like binding profile of MJ 14594 clearly show that the pharmacological activity of this antipsychotic compound differs from buspirone and related compounds.

According to the pharmacological profile established by the aforementioned tests, this compound of Formula (I) has promising potential as an antipsychotic agent. Thus, another aspect of the instant invention concerns a process for ameliorating a psychotic state in a mammal in need of such treatment which comprises systemic administration to said mammal of an effective dose of a formula (I) compound or a pharmaceutically acceptable acid addition salt thereof. On the basis of animal pharmacology, an effective oral dose could be expected to be from about 5 to 50 mg/kg and an effective parenteral dose could be expected to be somewhat lower, in the range of about 1 to 10 mg/kg body weight. Although the dosage and dosage regimen must in each case be carefully adjusted, utilizing sound professional judgment and considering the age, weight and condition of the recipient, the route of administration and the nature and gravity of the illness, generally the daily dose will be from about 1 to about 15 mg/kg, preferably 5 to 15 mg/kg, when administered parenterally and from about 5 to 50 mg/kg, preferably 10 to 40 mg/kg, when administered orally. In some instances, a sufficient therapeutic effect can be obtained at lower doses while in others, larger doses will be required.

The term systemic administration as used herein refers to oral, rectal, and parenteral (i.e., intramuscular, intravenous, and subcutaneous) routes. Generally, it will be found that when the compound of the present invention is administered orally, which is the preferred route; a larger quantity of the active agent is required to produce the same effect as a smaller quantity given parenterally. In accordance with good clinical practice, it is preferred to administer the instant compound at a concentration level that will produce effective antipsychotic effects without causing any harmful or untoward side effects.

Therapeutically, the instant compound can be generally given as pharmaceutical compositions comprised of an effective antipsychotic amount of MJ 14594 or a pharmaceutically acceptable acid addition salt thereof and a pharmaceutically acceptable carrier. Pharmaceutical compositions for affecting such treatment will contain a major or minor amount, e.g. from 95 to 0.5% of the compound of the present invention in combination with a pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a pre-determined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the predetermined dosage regimen, usually a whole, half, third, or quarter of the daily dosage administered once, twice, three or four times a day. Other therapeutic agents can also be present. Pharmaceutical compositions which provide from about 1 to 500 mg of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragecanth, or polyvinyl pyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch), and wetting agents, (e.g. sodium lauryl sulfate. Solutions or suspension of MJ 14594 with conventional pharmaceutical vehicles may be employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethyleneglycols or mixtures thereof. The polyethyleneglycols consist of a mixture of nonvolatile, normally liquid, polyethyleneglycols which are soluble in both water and organic liquids and which have molecular weights from about 200 to 1500.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in °C. when not specified.

The nuclear magnetic resonance (NMR) spectral characteristics refer to chemical shifts ($\delta$) expressed as parts per million (ppm) versus tetamethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiple (m), or doublet (d). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluant. The elemental analyses are reported as percent by weight.

SYNTHESIS OF INTERMEDIATES

Example 1

2-Chloro-5-fluoro-4-methylthiopyrimidin-2-one (IV)

5-Fluoro-4-thiouracil. A mixture of 5-fluorouracil (26 g, 0.12 mole) and phosphorus pentasulfide (45 g, 0.2 mole) in 500 mL dioxane was heated under reflux for 3 hr. The hot reaction mixture was filtered and concentrated in vacuo. The residue was dissolved in 650 mL water, heated with 5 g charcoal and filtered. The solid which crystallized on cooling was collected by filtration to yield 25.4 g (88%) of 5-fluoro-4-thiouracil, m.p. 269°–272° C.

5-Fluoro-4-methylthiopyrimidin-2-one. To a solution of 5-fluoro-4-thiouracil (25.4 g, 0.174 mole) in 350 mL 0.15N NaOH was added dropwise methyl iodide (59.4 g, 0.348 mole). The mixture was stirred at room temperature for 2 hr, cooled in ice and filtered. The collected solid was triturated with hot methanol to afford 18.5 g (66%) of the product, m.p. 205°–207° C.

A mixture of 5-fluoro-4-methylthiopyrimidin-2-one (21.1 g, 0.132 mole) phosphorus oxychloride (126.4 g, 0.824 mole) and N,N-dimethylaniline (27.0 g, 0.224 mole) was heated at reflux for 2 hr. The mixture was cooled in ice bath while ice was added to the reaction mixture followed by extraction with ether. The ether extract was dried (MgSO$_4$) and evaporated to a residue which was taken up in two 100 mL portions of hot Skelly B. The Skelly B supernatant was decanted from insoluble material, treated with charcoal, filtered and concentrated to provide 20.8 g (88%) of IV.

Example 2

8-[4-(Piperazinyl)butyl]-8-azaspiro[4.5]decane-7,9-dione (V)

A mixture of 3,3-tetramethyleneglutarimide (50.2 g, 0.3 mole), 1,4-dibromobutane (130 g, 0.6 mole) and anhydrous K$_2$CO$_3$ (06.7 g, 0.7 mole) in 500 mL toluene was heated at reflux for 20 hr, filtered and concentrated in vacuo. The residue was distilled (165°–170° C./0.01 mM) to give 64.1 g of 8-[4-(1-bromo)butyl]-8-azaspiro[4.5]decane-7,9-dione which was combined with piperazine (90.4 g, 1.05 mole) and K$_2$CO$_3$ (145.5 g, 1.05 mole) in 900 mL toluene and heated at reflux for 18 hr, filtered and concentrated in vacuo. The residue was distilled (180°–200° C./0.01 mM) to yield 52.7 g (82%) of V.

Example 3

8-[4-[4-(5-Fluoro-2-pyrimidinyl)-1-piperazine]butyl]-8-azaspiro[4.5]decane-7,9-dione Hydrated (I, MJ 14594-3)

A mixture of IV (4.47 g, 0.025 mole), V (7.7 g, 0.025 mole), $K_2CO_3$ (10.37 g, 0.07 mole) and KI (catalytic amount) in 100 mL acetonitrile was heated at reflux for 18 hr. The mixture was filtered, concentrated in vacuo and the residue chromatographed on 230 g silica gel using 2% ethanol-chloroform as eluant. Solvent removal gave 9.0 g (80%) of 8-[4-[4-[5-fluoro-4-(methylthio)-2-pyrimidinyl]-1-piperazinyl]butyl]-8-azaspiro[4.5]decane-7,9-dione.

A 3.5 g portion (0.008 mole) and moist Raney Nickel catalyst (1.5 tsp.) in 70 mL ethanol was heated at reflux for 3 hr, filtered and the solvent evaporated. The residue was heated in acetonitrile, filtered and concentrated in vacuo. This residue was then heated on a steam bath with Skelly B, the supernatant decanted from insoluble material and cooled to afford 1.8 g (59%) of I in hydrated form, m.p. 83°–85° C.

Anal. Calcd. for $C_{21}H_{30}FN_5O_2 \cdot 0.1H_2O$: C, 62.23; H, 7.51; N, 17.28. Found: C, 62.17; H, 7.46; N, 16.88.

Example 4

The Hydrochloride Salt of MJ 14594

The hydrochloride salt of I was obtained following a modification of the above procedure in which 8-[4-[4-[5-fluoro-4-(methylthio)-2-pyrimidinyl]-1-piperazinyl]-butyl]-8-azaspiro[4.5]decane-7,9-dione (9.0 g, 0.02 mole) and Raney Nickel (10–15 g) in 200 mL ethanol was heated at reflux 6 hr, filtered and concentrated. Water (50 mL) was added, the mixture basified with 50% NaOH and extracted with ether. The dried ($MgSO_4$) extract was evaporated, the residue dissolved in 20 mL ethanol and treated with 2.15 mL 7N ethanolic HCl to give 5.6 g (64%) of MJ 14594 hydrochloride, m.p. 224°–226° C.

Anal. Calcd. for $C_{21}H_{30}FN_5O_2 \cdot HCl$: C, 57.34; H, 7.12; N, 15.92. Found: C, 57.42; H, 7.15; N, 15.66.

NMR (DMSO-$d_6$): 1.50 (12,m); 2.61 (4,s); 3.02 (4,m); 3.50 (4,m), 3.64 (2,-[6.9 Hz]); 4.54 (2,m); 8.51 (2,s); 11.70 (1,bs).

IR (KBr): 790, 1110, 1250, 1350, 1490, 1560, 1670, 1750, 2600, 2935 and 2950 $cm^{-1}$.

What is claimed is:

1. The compound of Formula (I), 8-[4-[4-(5-fluoro-2-pyrimidinyl)-1-piperazine]butyl]-8-azaspiro[4.5]decane-7,9-dione, and pharmaceutically acceptable acid addition salts thereof

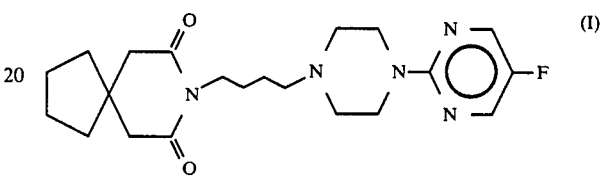

2. The process for eliciting an antipsychotic effect in a psychotic mammal which comprises administration to said mammal of a non-toxic but effective antipsychotic dose of the compound of Formula (I) of claim 1 or a pharmaceutically acceptable acid addition salt thereof.

3. A pharmaceutical composition in dosage unit form suitable for systemic administration to a mammalian host comprising a pharmaceutical carrier and a compound of Formula (I) of claim 1 or a pharmaceutically acceptable acid addition salt thereof.

* * * * *